United States Patent
Lieberman et al.

(10) Patent No.: US 7,874,672 B2
(45) Date of Patent: Jan. 25, 2011

(54) METHOD AND APPARATUS FOR UNIVERSAL IMPROVEMENT OF VISION

(75) Inventors: David M. Lieberman, New York, NY (US); Jonathan Grierson, Atwater, OH (US)

(73) Assignee: Scientific Optics, Inc., New York, NY (US)

( * ) Notice: Subject to any disclaimer, the term of this patent is extended or adjusted under 35 U.S.C. 154(b) by 29 days.

(21) Appl. No.: 12/201,710

(22) Filed: Aug. 29, 2008

(65) Prior Publication Data

US 2009/0048670 A1 Feb. 19, 2009

Related U.S. Application Data

(63) Continuation of application No. PCT/US2007/063572, filed on Mar. 8, 2007.

(60) Provisional application No. 60/780,153, filed on Mar. 8, 2006.

(51) Int. Cl.
- G02C 7/02 (2006.01)
- G02C 7/04 (2006.01)
- A61F 2/16 (2006.01)

(52) U.S. Cl. .................. 351/159; 351/160 R; 623/6.23

(58) Field of Classification Search .................. 351/159, 351/160 R, 160 H; 623/6.23, 6.24
See application file for complete search history.

(56) References Cited

U.S. PATENT DOCUMENTS

| | | | |
|---|---|---|---|
| 2,878,721 A | 3/1959 | Kanolt | |
| 5,800,532 A | 9/1998 | Lieberman | |
| 5,953,098 A * | 9/1999 | Lieberman et al. | 351/160 R |
| 6,099,522 A | 8/2000 | Knopp et al. | |
| 6,206,887 B1 * | 3/2001 | McDonald | 606/107 |
| 6,340,229 B1 * | 1/2002 | Lieberman et al. | 351/160 R |
| 6,533,416 B1 * | 3/2003 | Fermigier et al. | 351/160 R |
| 7,543,937 B2 * | 6/2009 | Piers et al. | 351/177 |
| 2003/0038920 A1 | 2/2003 | Lin | |
| 2005/0021137 A1 | 1/2005 | Blake et al. | |
| 2005/0177313 A1 | 8/2005 | Latkany | |
| 2005/0203619 A1 * | 9/2005 | Altmann | 623/6.23 |
| 2006/0038307 A1 * | 2/2006 | Sasai | 264/2.5 |
| 2006/0189966 A1 * | 8/2006 | Lieberman et al. | 606/12 |
| 2006/0203189 A1 * | 9/2006 | Ho et al. | 351/160 R |

FOREIGN PATENT DOCUMENTS

GB 2020847 A 11/1979

(Continued)

OTHER PUBLICATIONS

European Search Report and Written Opinion for PCT/US2007063572, filed Apr. 29, 2009.

*Primary Examiner*—Jordan M. Schwartz
(74) *Attorney, Agent, or Firm*—Kaplan Gilman & Pergament LLP

(57) ABSTRACT

"Universal improvement" of vision is achieved by effectively changing the shape of the anterior refracting surface of the cornea to an ideal "turtleback" shape, on which is imposed the necessary curvature adjustment to achieve correction of distance vision. In accordance with one embodiment, the cornea is actually formed to the turtleback shape through corneal surgery, preferably laser ablation surgery. In accordance with a second embodiment, a contact lens with the desired distance corrected ideal turtleback shape on its anterior surface is positioned over the cornea.

17 Claims, 13 Drawing Sheets

FOREIGN PATENT DOCUMENTS

| | | |
|---|---|---|
| WO | 9966366 A | 12/1999 |
| WO | 0125837 A1 | 4/2001 |
| WO | 02083078 A | 10/2002 |
| WO | 03041616 A | 5/2003 |
| WO | 2004023189 A | 3/2004 |
| WO | 2006004440 A | 1/2006 |

* cited by examiner 0.33mm Center Point Spread

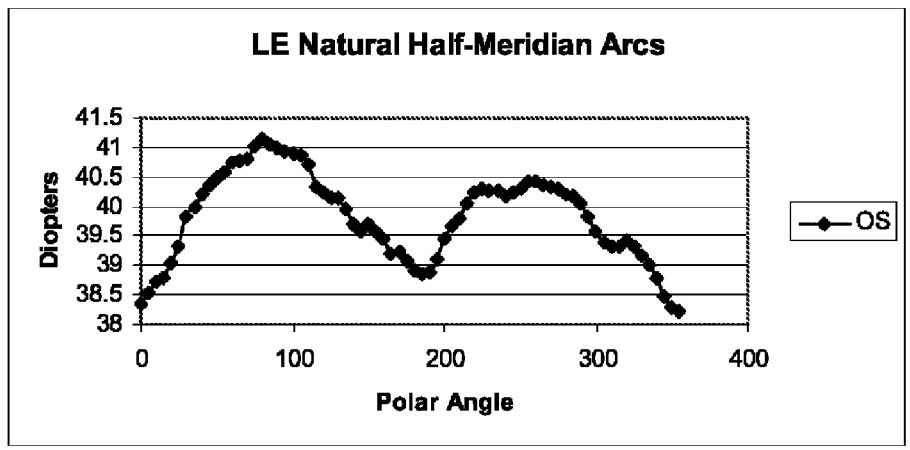
(A)
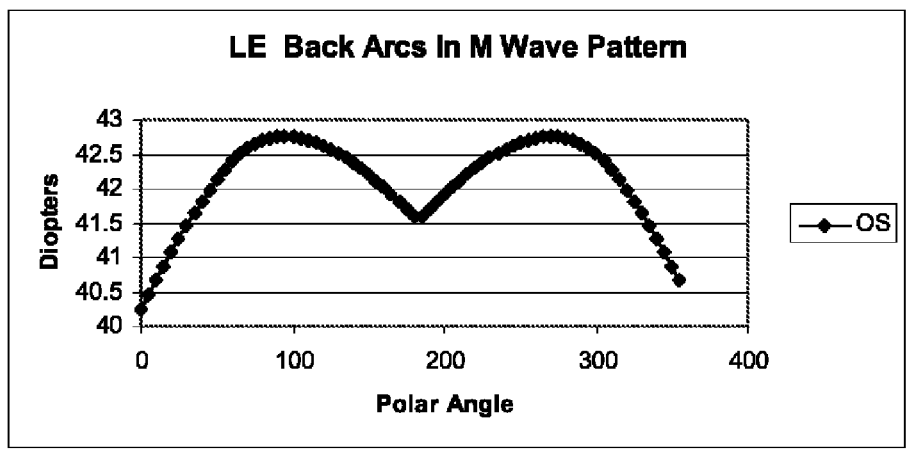
(B)
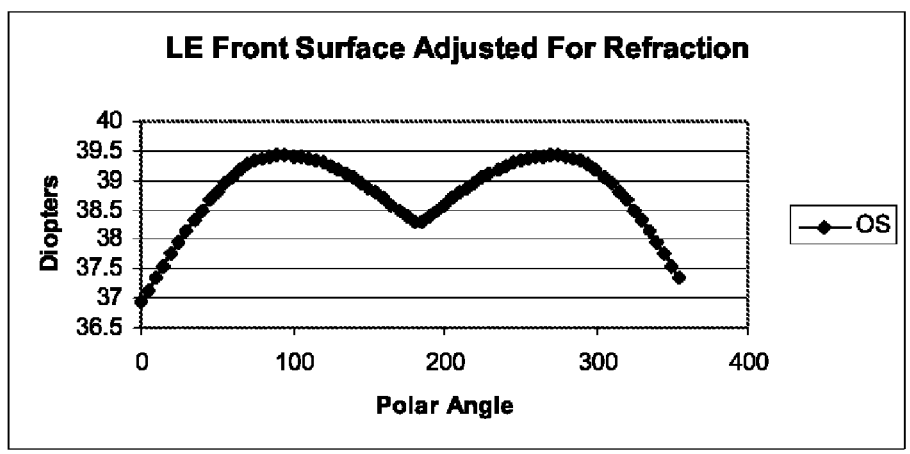
(C)
Fig. 16

METHOD AND APPARATUS FOR UNIVERSAL IMPROVEMENT OF VISION

CROSS-REFERENCE TO RELATED APPLICATIONS

This application claims the benefit of U.S. Provisional Patent Application Ser. No. 60/780,153 filed Mar. 8, 2006 the entirety of the disclosure of which application is incorporated herein by reference. This application is a continuation of International Application No. PCT/US0763572, filed Mar. 8, 2007, and was published in English on Sep. 13, 2007 under No. WO 2007/104013.

BACKGROUND OF THE INVENTION

The present invention relates generally to a method and apparatus for improving the vision of an eye, and, more particularly concerns a method and apparatus that improve vision at all distances, hereafter referred to as "universal improvement."

Most common defects in human vision are caused by the inability of the eye to focus incoming light to a common focal point on the retina. For example, nearsightedness can be attributed to an eye which focuses light anterior to the retina, farsightedness can be attributed to an eye which focuses incoming light posterior to the retina, and astigmatism can be attributed to an eye which does not have a common focal point. Human optical scientists frequently model the cornea as a portion of an ellipsoid defined by orthogonal major and minor axes.

Today, vision is commonly improved in one of two ways: either a lens is placed in front of the eye (e.g. a contact lens or a spectacle lens) or within the eye (e.g. an intraocular lens) to refocus incident light into the eye appropriately. Alternatively, the effective external surface shape of the cornea is changed, as by laser ablation surgery or other surgical means to alter the anterior surface shape of the cornea. Such surgical procedures for correcting visual acuity are typically directed at increasing or decreasing the surface curvature of the cornea. Some procedures are intended to make the corneal shape more spherical, and others are intended to change the corneal shape to an "average" ellipse, or more recently to making corrections based on wavefront analysis, a methodology that is intended to correct for the "higher order aberrations" of the eye.

Contact lenses or spectacles are used to provide vision correction for objects of regard at different distances from the eye, for example objects relatively close to the eye or for objects remotely displaced from the eye. In this regard, different zones of a lens have been provided with different lens powers so as to permit the wearer to see objects at different distances. The traditional "multifocal" contact lens is one wherein there are power differences located in different areas or zones on the surface of the lens. Such zones have been designed as spherical segments and spherical lunes of different power formed on the lens. Although such lenses have provided vision correction at certain distances, they have not provided sufficient universal vision improvement to restore natural visual acuity for an eye that requires multiple levels of depth correction in addition to the distance refractive error. In addition, variable focus spectacle lenses have been provided in which a central optical region is formed with a curvature that varies continuously with vertical position, to provide vision correction at all distances. However, the wearer must raise or lower his head to make an adjustment for distance. Some contact lens designs provide two or more zones of refractive power in distinct bands on the anterior surface. This lens translates in position depending on lid position. In order to provide clear vision with the translating design, the wearer must, similarly, raise or lower his head in order to adjust for the distance of the object being viewed. It is less than optimal to require the wearer to make such adjustments.

It would be desirable to provide universal vision improvement without the need for any extraneous physical movements by the wearer.

SUMMARY OF THE INVENTION

Making use of the analysis of clinical measurements in accordance with the surface modeling techniques disclosed in U.S. Pat. No. 5,807,381 the applicants have discovered that the cornea of an eye which has an ideal "turtleback" shape will exhibit universal improvement in vision if its surface curvature is modified to correct only for defective distance vision. As used herein, a "turtleback" shape will be understood to exhibit the flattest surface curvature at a point lying at the edge closest to the nose, where surface curvature is determined along a half-meridian from that point to a central point on the cornea. Moving upwardly and about the perimeter of the cornea, the surface curvature will increase continuously until it reaches a maximum at the vertical extreme of the cornea. The surface curvature will then decrease continuously until it reaches an intermediate value at the edge of the cornea most distant from the nose, will increase continuously to a maximum at the vertically lowermost edge of the cornea, and will decrease continuously until it returns to its minimum at the edge of the cornea closest to the nose.

In accordance with the present invention, universal improvement of vision is achieved by effectively changing the shape of the cornea to an ideal turtleback shape, on which is imposed the necessary curvature adjustment to achieve vision correction for distant objects of regard. In accordance with one embodiment, the cornea is actually formed to the desired shape through corneal surgery, preferably laser ablation surgery. In accordance with a second embodiment, a contact lens with the desired distance vision and adjusted ideal turtleback shape on its anterior surface is positioned over the cornea.

BRIEF DESCRIPTION OF THE DRAWINGS

The foregoing brief description and further objects, features and advantages of the present invention will be understood more completely from the following detailed description of presently preferred embodiments, with reference being had to the accompanying drawings in which:

FIG. 16 illustrates three waveforms useful in describing the ideal turtleback shape adjustment to the cornea that provides universal vision improvement

DETAILED DESCRIPTION OF THE PREFERRED EMBODIMENTS

Figure 1:
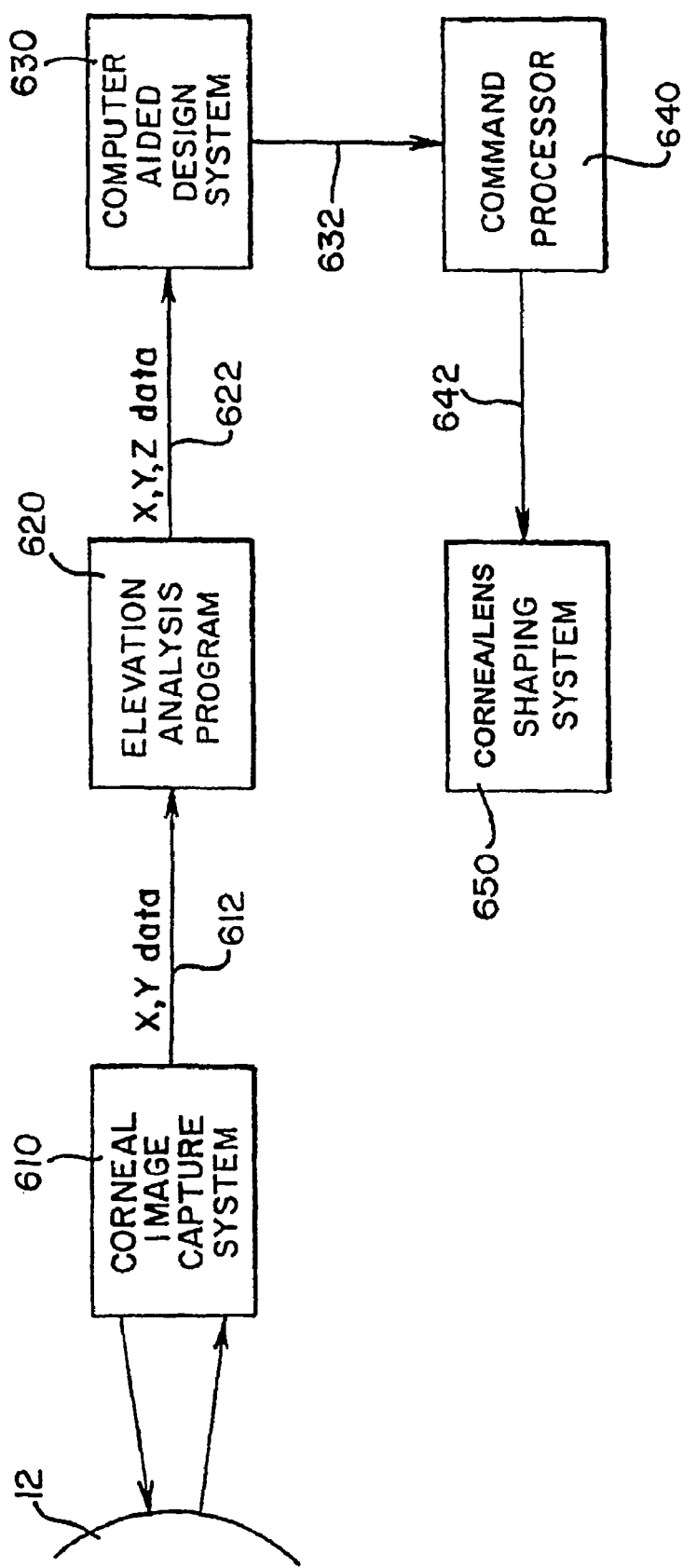
FIG. 1 is a block diagram illustrating a method for achieving vision correction in accordance with the present invention through either laser ablation of the cornea or an appropriately shaped corrective lens.

In conjunction with modern corneal procedures, such as corneal ablation surgery, for clinical applications, and for contact lens design and manufacture, high resolution cameras are used to obtain a digitized array of discrete data points on the corneal surface. One system and camera which have been available for mapping the cornea is the PAR Corneal Topography System (PAR CTS) of PAR Vision Systems. The PAR CTS maps the corneal surface topology in three-dimensional Cartesian space, i.e., along x- and y-coordinates as well as depth (Z) coordinate.

The "line-of-sight" is a straight line segment from a fixation point to the center of the entrance pupil. As described more fully in Mandell, "Locating the Corneal Sighting Center From Videokeratography," J. Refractive Surgery, V. 11, pp. 253-259 (July/August 1995), a light ray which is directed toward a point on the entrance pupil from a point of fixation will be refracted by the cornea and aqueous humor and pass through a corresponding point on the real pupil to eventually reach the retina.

The point on the cornea at which the line-of-sight intersects the corneal surface is the "optical center" or "sighting center" of the cornea. It is the primary reference point for refractive surgery in that it usually represents the center of the area to be ablated in photorefractive keratectomy. The line-of-sight has conventionally been programmed into a laser control system to govern corneal ablation surgery. However, some surgeons prefer to use the pupillary axis as a reference line. Other surgeons center the ablation profile about the corneal apex usually defined as the area on the cornea of greatest curvature change. Experienced practitioners have employed various techniques for locating the sighting center. In one technique, the angle lambda is used to calculate the position of the sighting center relative to the pupillary ("optic") axis. See Mandell, supra, which includes a detailed discussion of the angles kappa and lambda, the disclosure of which is incorporated herein by reference as if set forth in its entirety herein.

During the LASIK corneal ablation procedure a portion of the corneal surface is reflected and the ablation performed on the exposed surface. The gathered elevational data is used to direct an ablation device, such as a laser, so that the corneal surface can be selectively ablated to more closely approximate a spherical surface of appropriate radius about the line-of-sight, or an "average" ellipse, or a wavefront fingerprint within the ablation zone. The use of the line-of-sight as a reference line for the procedures may reduce myopia or otherwise correct a pre-surgical dysfunction or a visual abnormality. However, a more irregularly shaped cornea may result, which may exacerbate existing astigmatism or introduce astigmatism or spherical aberration in the treated eye. This will complicate any subsequent vision correction measures that need be taken. Also, any substantial surface irregularities which are produced can cause development of scar tissue or the local accumulation of tear deposits, either of which can adversely affect vision.

Implicit in the use of the-line-of sight or the pupillary axis as a reference axis for surgical procedures is the assumption that the cornea is symmetric about an axis extending along a radius of the eye. The cornea, however, is an "asymmetrically aspheric" surface.

"Aspheric" means that the radius of curvature along any corneal "meridian" is not a constant (a "meridian" could be thought of as the curve formed by the intersection of the corneal surface and a plane containing the pupillary axis). Indeed, the corneal curvature tends to flatten progressively from the geometric center to the periphery. "Asymmetric" means that the corneal meridians do not exhibit symmetry about their centers. The degree to which the cornea is aspheric and/or asymmetrical varies from patient to patient and from eye to eye within the same person.

Analysis of clinical measurements in accordance with the surface modeling techniques of U.S. Pat. No. 5,807,381 reveals that the point on the surface of the cornea which is most distant from the reference plane of the PAR CTS (hereafter referred to as the HIGH point) is a far more effective reference point for corneal ablation and lens design than the center of the cornea or the pupillary center. Specifically, as demonstrated in U.S. Pat. No. 5,807,381 laser ablation about an axis passing through the HIGH point produces a much more regularly shaped cornea and removes less corneal material than the same operation performed about an axis close to the center of the eye, such as the pupillary axis.

Analysis of clinical measurements in accordance with the methods of U.S. Pat. No. 5,807,381, and International Application No. PCT/US03/1763 (published as WO03/101341), the disclosures of which are incorporated herein by reference in their entireties, raises questions about assumptions that have been made about the structure of the human cornea which are inherent in such well-known corneal analysis technologies as wave-front analysis and Placido disc technology. In particular, it was found that, unlike other optical systems, the central portion of the cornea (for example, out to a 3 mm diameter) is not necessarily optically superior to substantially greater portions of the cornea (for example, out to a 7 mm diameter) in its ability to focus. The central portion of the cornea exhibits a great deal of focus scattering. That is, different regions on the cornea do not focus to the same point on a focal axis. Indeed, they do not even focus on the same axis. This focus difference is usually most pronounced in the central portion of the cornea and decreases substantially at increasing diameters from the center.

As disclosed in PCT/US03/1763, vision can be improved by adjusting the focus of the cornea, referred to herein as "orthogonalizing," so that different regions focus substantially to the same axis. This can be accomplished by shaping the cornea (e.g., through ablation) or by applying an appropriate corrective lens, effectively reducing radial and axial focus scatter. An additional benefit of orthogonalization for many patients was that presbyopia (defective near vision) was substantially reduced. That is, many presbyopic patients fitted with orthogonalized contact lenses that did not have components that focused at different distances could achieve simultaneous improvement in near and distance vision. However, sufficient improvement could not be achieved in both distance and near vision to provide universal improvement for most near sighted individuals with substantial age related defects in near vision, as is very common.

A process for achieving laser ablation of the cornea and contact lens shaping in accordance with the present invention is illustrated in block diagram form in FIG. 1. The process makes use of a Corneal Image Capture System 610, an Elevation Analysis Program 620, a Computer Aided Design System 630, a Command Processor 640 and a Cornea Shaping System 650. The Corneal Image Capture System 610, in conjunction with the Elevation Analysis Program 620, generates a three dimensional topographic map of the cornea of the patient. The Computer Aided Design System 630 is used as an aid in editing or modifying the corneal topographic data, to create a surface model, and data relating to the model is sent to a Cornea Shaping System 650 via the Command Processor 640. The Command Processor 640 uses the topographic data describing the surface of the cornea to be shaped from the Computer Aided Design System 630 to generate a sequence of commands/control signals required by the Cornea/Lens Shaping System 650. The Cornea/Lens Shaping System 650 accepts, from the Command Processor 640, a sequence of commands that describe the three dimensional movements of the Cornea/Lens Shaping System (any coordinate system may be used; e.g., Cartesian, radial or spherical coordinates) to shape the cornea or machine (e.g., a lathe) manufacturing a contact lens.

The Corneal Image Capturing System 610 and the Elevation Analysis Program 620 are preferably components of the PAR® Corneal Topography System ("the PAR® System"), which is available from PAR Vision Systems. The Elevation Analysis Program 620 is a software program executed by a processor, for example an IBM™ compatible PC. Program 620 generates a third dimension element (a Z coordinate representing distance away from a reference plane inside the eye) for each of a plurality of sample points on the surface of the cornea measured by system 610. Each point is defined by its X-Y coordinates as mapped into the reference plane, and its Z coordinate is determined from brightness of the point. One method of calculating the elevation of each point, i.e., the Z coordinate, is by comparing the X-Y and brightness values measured from the patient's cornea 14 with the coordinates and brightness of some reference surface with known elevation, e.g., a sphere of a known radius. The reference values can be pre-stored.

The final output of the Elevation Analysis Program 620 is the X-Y-Z coordinates for a multiplicity of sample points, commonly known as a point cloud, on the surface of the cornea 14. It will be apparent to those skilled in the art that any method can be used that can generate X, Y, Z corneal data providing both location and elevation information for points on the corneal surface with the required accuracy. In the preferred embodiment about 1200 points are spaced in a grid pattern, as viewed in the X-Y plane, so the projections of the points into the X-Y plane are about 200 microns apart.

The X-Y-Z data output from the Elevation Analysis Program 620 can be formatted in any number of well-known machine-specific formats. Preferably, the data are formatted in Data Exchange File (DXF) format, an industry standard format which is typically used for the inter-application transfer of data. A DXF file is an ASCII data file, which can be read by most computer aided design systems.

Figure 2:
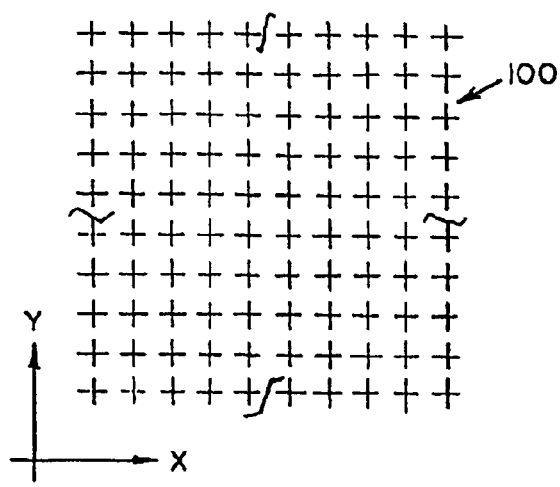
FIG. 2 is a schematic diagram illustrating a plan view of a point cloud as obtained with a corneal image capture system.
Figure 3:
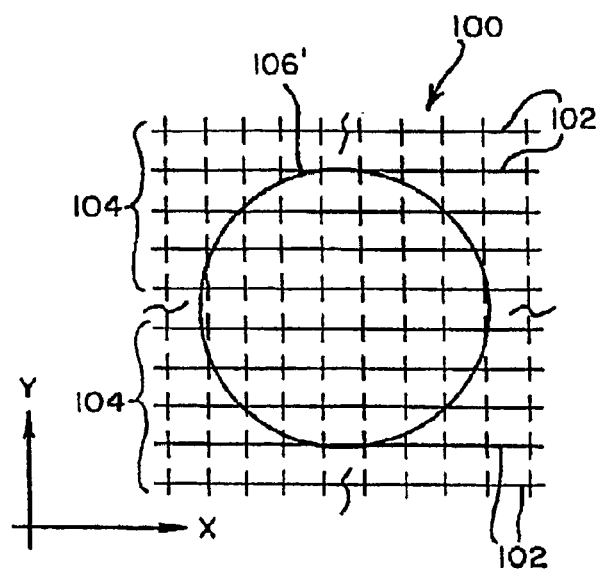
FIG. 3 is a schematic plan view similar to FIG. 2 illustrating a plurality of splines and how they are connected through the data points of the point cloud.

Referring now to FIGS. 2 and 3, a point cloud 100 is depicted as it would appear when viewing the reference plane along the Z-axis (i.e., as projected into the X-Y plane). Each point corresponds to a particular location on the patient's cornea. The data are usually generated from an approximately 10 mm×10 mm bounded area of the cornea, the working area.

Thus, there may be as many as 50 rows of data points. A surface 108 (see FIG. 4) that models or matches the topography of the surface of the patient's cornea is generated by the computer aided design system 630 from the data points generated by the Elevation Analysis Program. In a preferred embodiment, Computer Aided Design System 630 is the Anvil 5000™ program which is available from Manufacturing Consulting Services of Scottsdale, Ariz.

Cornea matching surface 108 is preferably produced by first generating a plurality of splines 102, each defined by a plurality of the data points of the point cloud 100. The generation of a spline that intersects a plurality of data points (i.e., knot points) is, per se, known to those skilled in the art and can be accomplished by the Anvil 5000™ program once the input data have been entered. For more information regarding the generation of a surface model, see U.S. Pat. No. 5,807,381, the disclosure of which is incorporated herein by reference. In a preferred embodiment, the known non-uniform rational B-spline formula is used to generate the splines, but they could be generated by other well-known mathematical formulas for splines, such as the cubic spline formula or the rational uniform B-spline formula. As illustrated in FIG. 3, in a preferred embodiment, each of the splines 102 lies in a plane that is parallel to the X and Z axes and includes a row of points from the cloud 100 in FIG. 3.

Surface 108, which matches the corneal surface of the scanned eye, is then generated from splines 102. There are a number of well-known mathematical formulas that may be used to generate a surface from a plurality of splines 102. In the preferred embodiment, the well known nurb surface equation is used to generate a corneal surface from splines 102. In the embodiment, because the scanned area of the eye is approximately 10 mm×10 mm, approximately 50 splines 102 are created. As illustrated in FIG. 3, a skinned surface segment 104 is created for a small number (e.g., five) of the adjacent splines. Adjacent skinned surface segments 104 share a common border spline. Thus, about ten skinned surface segments are generated from the point cloud and are then merged together by the Anvil 5000™ program in a manner known to those skilled in the art, to produce one composite surface 108.

Neither the original data points, nor the knot points of splines 102 necessarily lie on-surface 108, owing to the mathematical generation of the surface when using the nurb surface equation formula. However, the surface 108 estimates those points within a predefined tolerance.

The HIGH point on the generated corneal matching surface 108 (i.e., the point having the greatest Z value) is determined. A cylinder 106 of a predetermined diameter is then projected onto the corneal matching surface 108 along an axis which is parallel to the Z-axis and passes through the HIGH point. Cylinder 106 preferably has a diameter of about 3 mm to about 8 mm, typically about 7 mm, and the closed contour formed by the intersection of cylinder 106 with surface 108 projects as a circle 106' in the X-Y plane. On the matching surface 108, this contour defines the outer margin 26 of the working area of the cornea. The cornea is the most symmetric and spherical about the HIGH point and, therefore, provides the best optics at this point.

The outer margin 26 must fit within the point cloud, so that the surfaces of the cornea can be formed based on the measured corneal data. The computer aided design system 630 can then illustrate a default circle 106' (in the X-Y plane) with respect to the point cloud, for example on a monitor screen, so that the operator can be assured that circle 106' falls within the point cloud. Additionally, system 630 can be set up to determine if circle 106' falls within point cloud 100 and, if it does not fall completely within point cloud 100, to alert the user to manipulate the circle (i.e., move the center point and/or change the radius of the circle) so that circle 106' lies within the corneal data point cloud 100. In a worst case scenario, the eye should be rescanned if insufficient data is available from the scanned eye to ensure that the working area of the cornea will fit properly within the point cloud. Alternatively, the area of the point cloud can be made larger.

It is to be understood that circle 106' is only a circle when viewed in the X-Y plane (i.e., looking along the Z-axis). Actually, the periphery 26 is approximately elliptical and lies in a plane which is tilted relative to the reference plane. A line Perpendicular to this tilted plane which passes through the HIGH point will be referred to as the "LOCAL Z-AXIS" or "tilted axis," and the tilt of the tilted plane relative to the reference plane will be considered the tilt angle of the working area of the cornea.

The cornea is about 600 μm thick. In most corneal ablation procedures, less than 100 μm depth of cornea is ablated because there is virtually no risk of scarring with the type of lasers that are typically used. Beyond the 100 μm depth, the risk of scar-like imperfections. For example, 120 μm depth ablation is known to cause scarring. However, there exists the possibility that the risk of scarring for surface ablations may be reduced by drug therapy prior to or contemporaneous with the laser treatment. However, most of today's laser surgery does not cause scarring, as most procedures are under the LASIK flap. The fear in LASIK is ablating too deep wherein the residual bed is less than ~250 μm. If the bed is less than this amount, structural failure can occur. The magnitude of the corneal undulations is typically about fifteen to twenty microns from the crest of a hill to the trough of a valley and may be as great as about thirty microns.

The surgical procedures performed in accordance with the present invention and optical lenses manufactured in accordance with the invention, will seek to correct the patient's vision in accordance with the required corrections established in a "refraction test." When this test is performed, the patient sits in chair which is fitted with a special device called a "phoropter," through which the patient looks at an eye chart approximately 20 feet away. As the patient looks into the phoropter, the doctor manipulates lenses of different strengths into view and, each time, asks the patient whether the chart appears more or less clear with the particular lenses in place. In practice, the doctor is able to vary the power or diopter correction about two orthogonal axes, as well as the degree of rotation of those axes about a Z-axis along the line-of-sight. The doctor continues to modify these three parameters until he achieves the optimum vision. The results of the refraction test are usually given in the form "a, b, c," where "a" is the diopter correction at the first axis, "b" is the additional diopter correction required at the second, orthogonal axis, and "c" is the angle of rotation of the first axis relative to the horizontal. This form of information is given for each eye and is immediately useful in grinding a pair of lenses for eyeglasses.

There will now be described a technique for generating characterizing curves on surface 108, which will be useful below. A plane 110 is constructed which contains the LOCAL Z-AXIS (See FIG. 4). The intersection between plane 110 and surface 108 defines a first characterizing curve 112. Plane 110 is then rotated about the LOCAL Z-AXIS, for example by a 5° increment counterclockwise, as represented by line 114, where its intersection with surface 108 defines a second characterizing curve 116, which is illustrated as a dashed line in FIG. 4. This process continues at fixed rotational increments about the LOCAL Z-AXIS, for example every 5°, until plane 110 has swept 360°, to produce a complete set of characterizing curves (meridians), in this case seventy-two (360° % 5°).

Each of these characterizing curves is then estimated by a best-fit spherical (circular) arc. One manner of doing this is simply to select a circular arc which passes through three known points for each curve (e.g., the point at which it touches the contour 106', the HIGH point, and that point which is halfway between those two points when viewed in projection along the local Z axis). Once the spherical arcs are generated, the focal point of a portion of the cornea represented by a circular arc can be estimated by the center of that arc. Techniques for locating the center of a spherical arc are well-known. The resulting set of arc centers then provides a representation of focus scattering.

Figure 5:
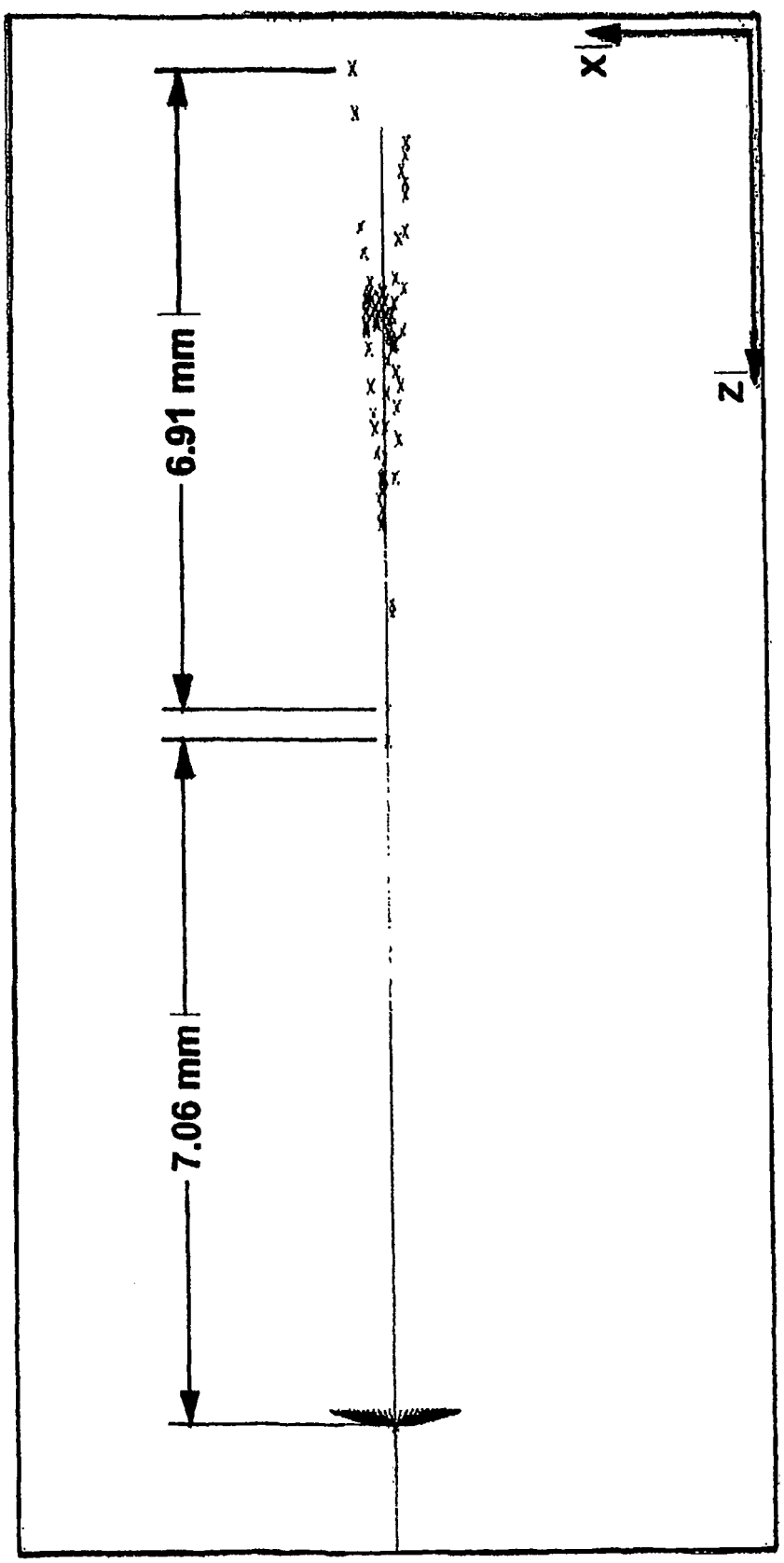
FIG. 5 is a diagram exemplifying the axial focus scatter of a cornea at a 3 millimeter diameter.
Figure 6:
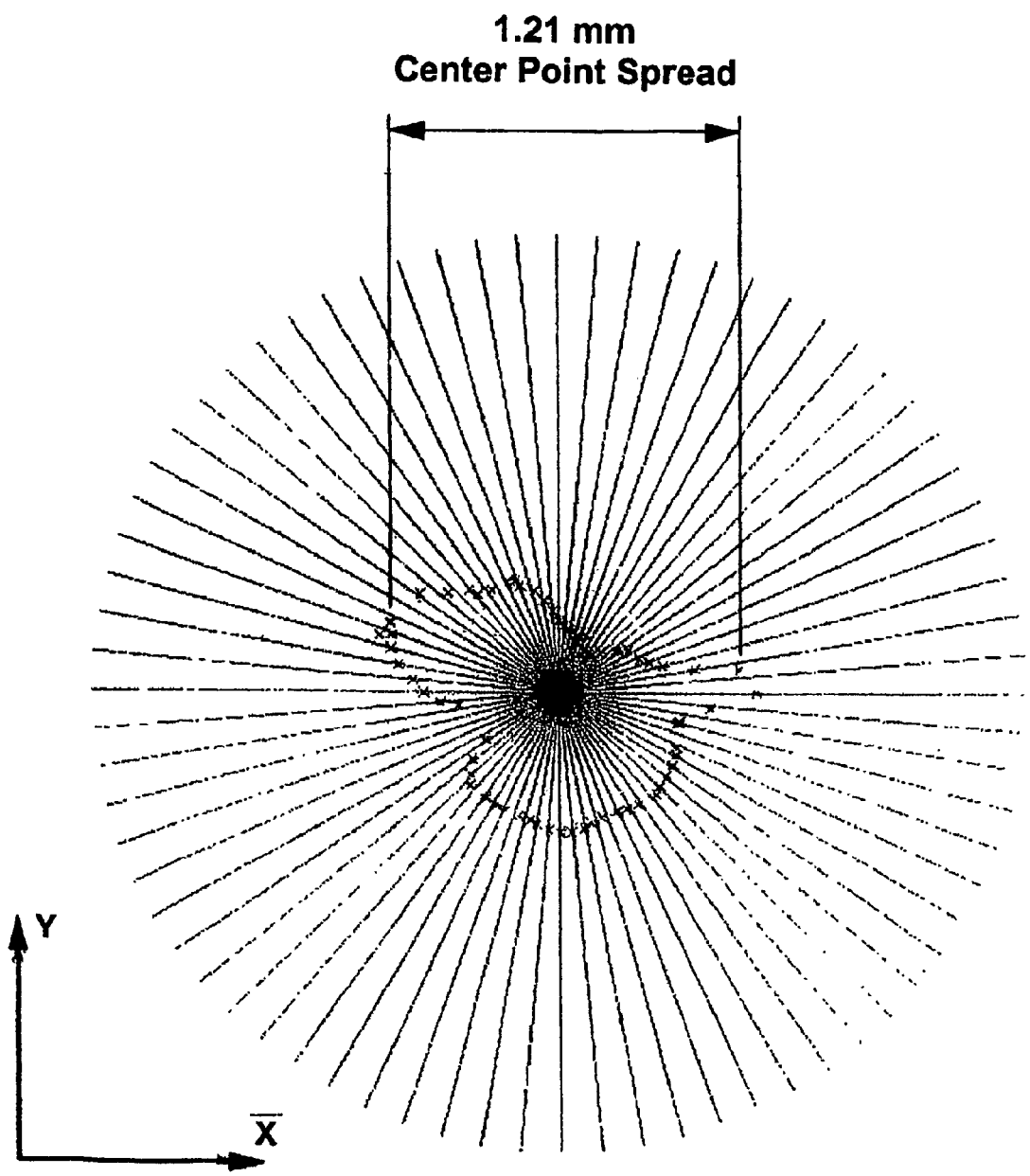
FIG. 6 illustrates the radial focus scatter corresponding to FIG. 5.
Figure 7:
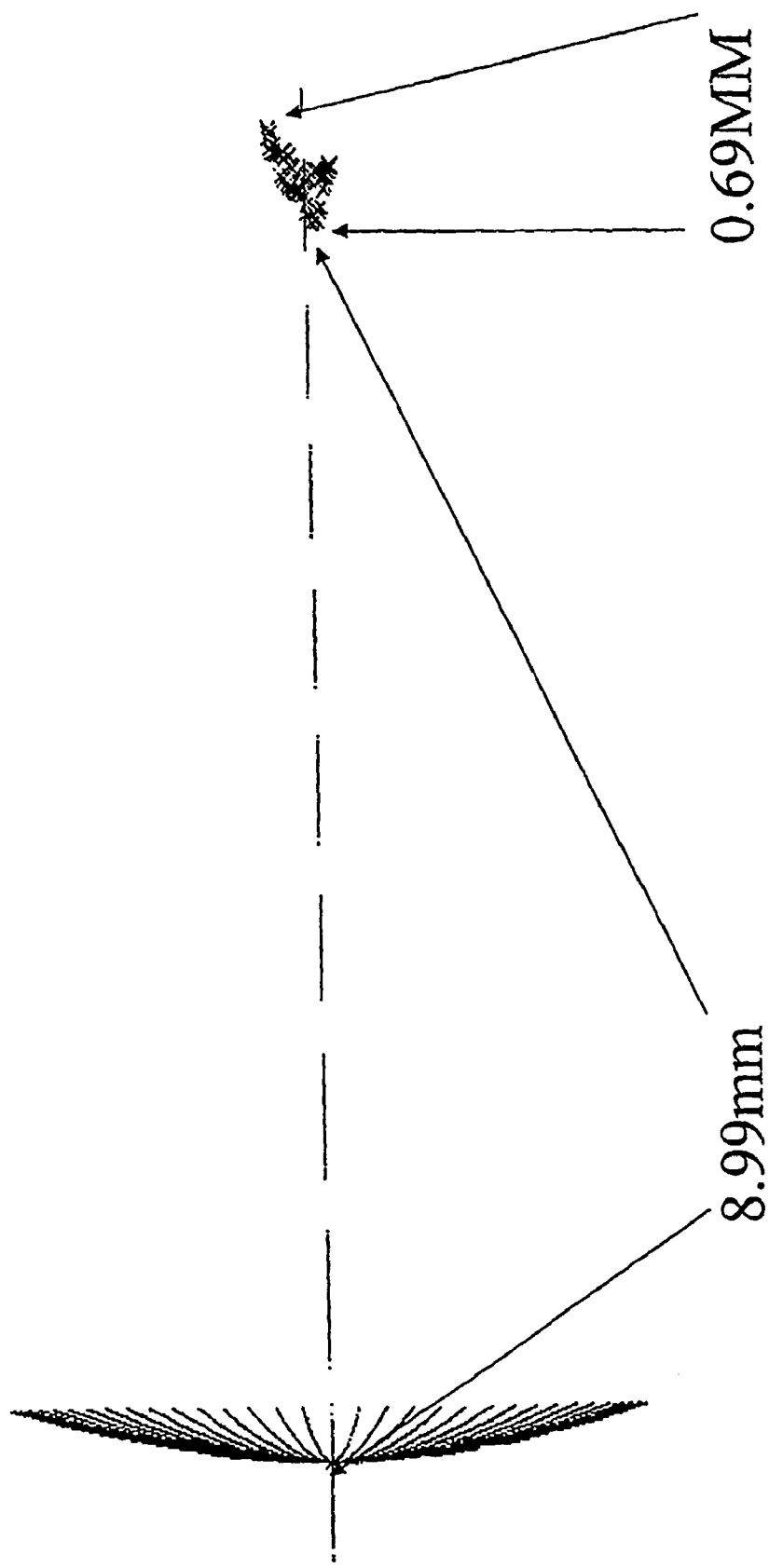
FIG. 7 is a diagram exemplifying the axial focus scatter of a cornea at a 5 millimeter diameter.
Figure 8:
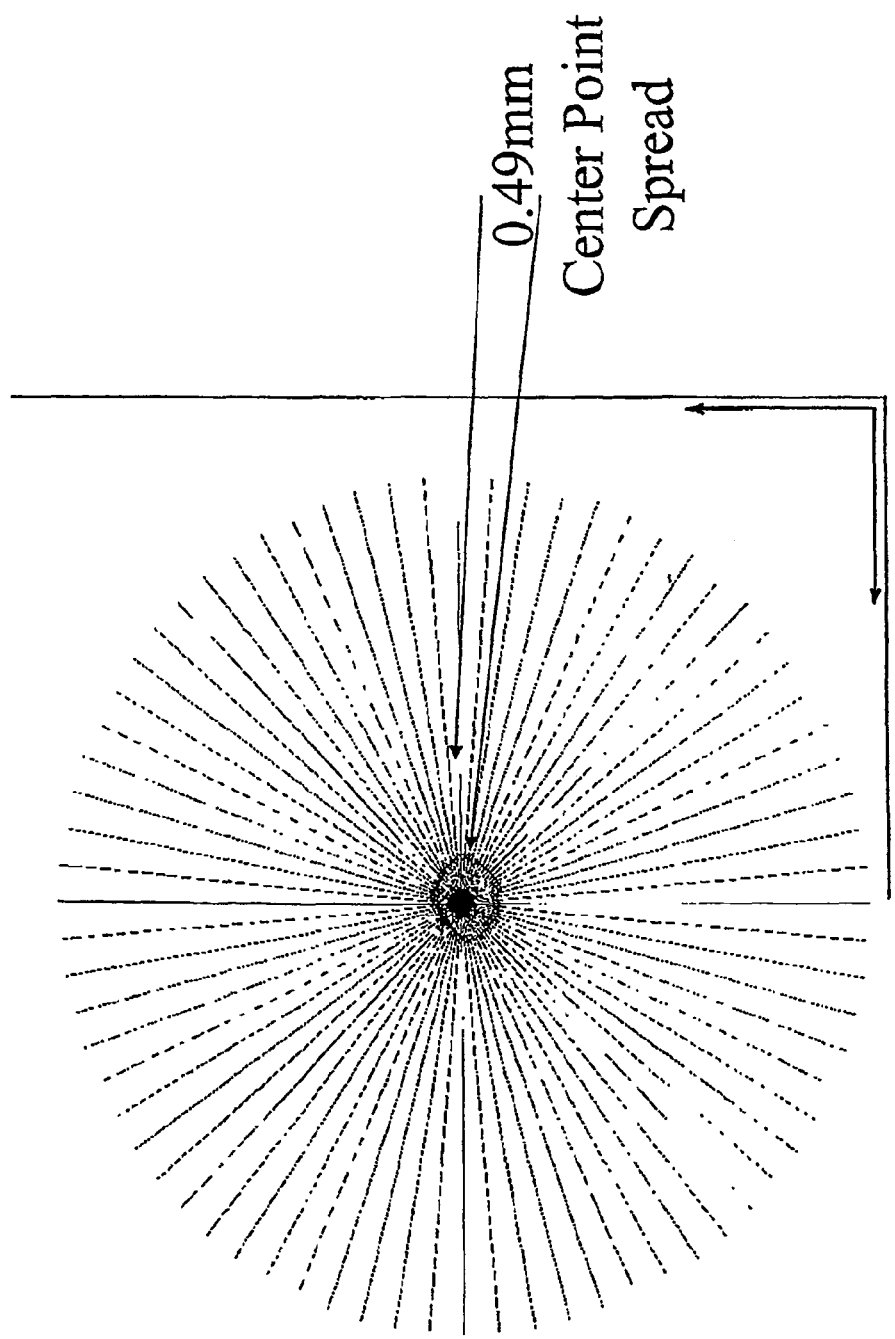
FIG. 8 illustrates the radial focus scatter corresponding to FIG. 7.
Figure 9:
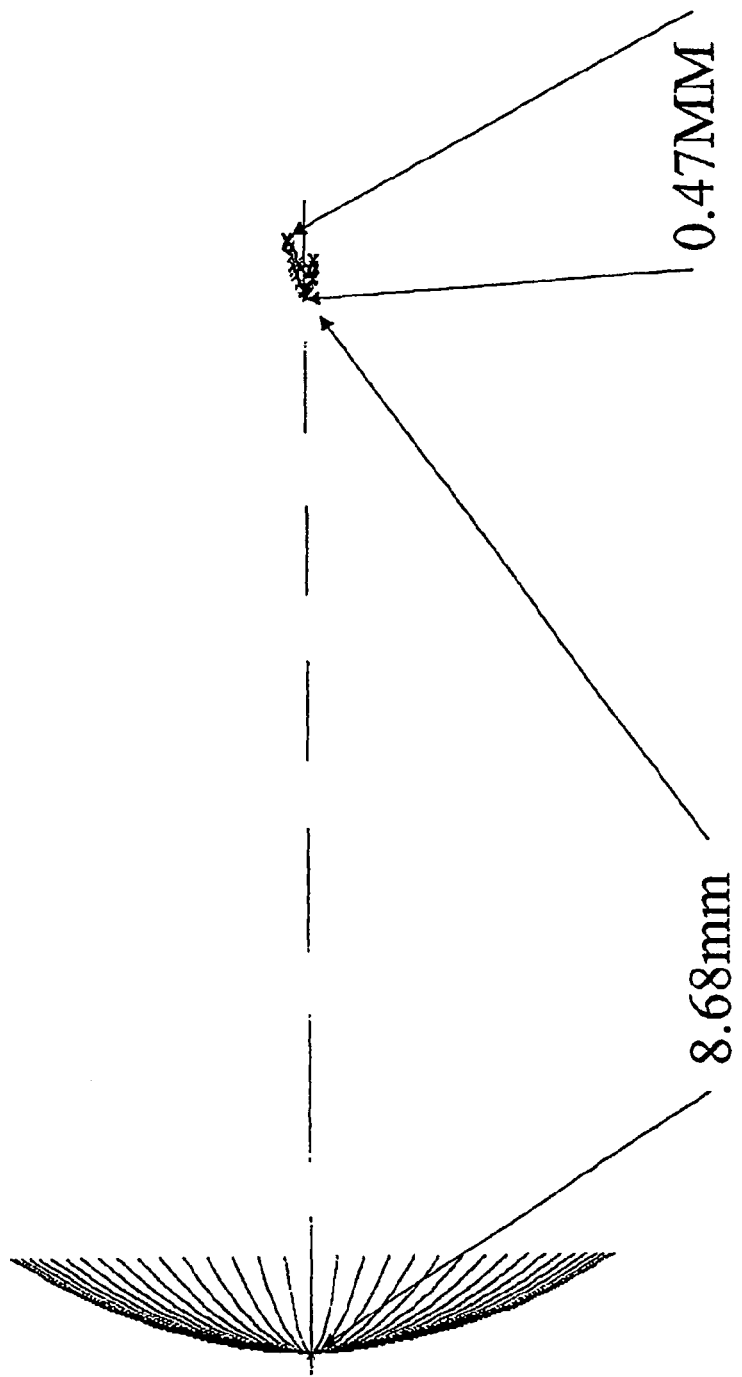
FIG. 9 is a diagram exemplifying the axial focus scatter of a cornea at a 7 millimeter diameter.
Figure 10:
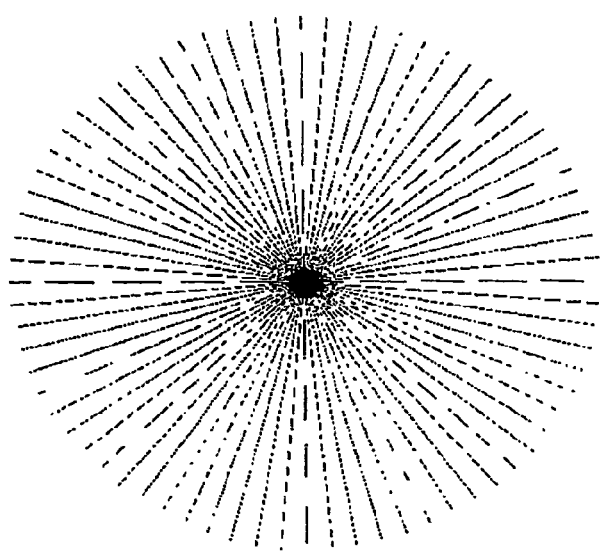
FIG. 10 illustrates the radial focus scatter corresponding to FIG. 9.

For purposes of illustration, the preceding procedure was performed on the corneal model of a patient having 20/15 uncorrected visual acuity. FIG. 5 is a focus scatter diagram along the LOCAL Z-AXIS for that portion of the cornea extending out to a 3.0 mm diameter. In this case, the focal points start at 7.06 mm along the LOCAL Z-AXIS and extend out an additional 6.91 mm. FIG. 6 illustrates that the radial scatter within a 3 mm diameter is 1.2 mm. Similarly, FIG. 7 illustrates that the axial focus scatter of a 5 mm diameter portion of the cornea begins at 8.99 mm and extends for an additional 1.69 mm. As shown in FIG. 8, the radial scatter of the same portion of the cornea is 0.49 mm. FIG. 9 illustrates that the axial focus scatter at 7 mm begins at 8.68 mm and extends axially for an additional 0.47 mm, whereas FIG. 10 illustrates that the corresponding radial scatter is 0.33 mm. Clearly, focus scatter is most severe in the central portion of the cornea, and decreases significantly as larger portions of the cornea are considered. Therefore, it would clearly be desirable to reduce or eliminate the focus scatter at least in central portions of the cornea. This can be accomplished by "orthogonalizing" at least a portion of the cornea. The term "orthogonalizing" refers to a re-shaping of the surface model so as to piecewise re-focus the cornea towards the LOCAL Z-AXIS. The re-shaped surface model can then be applied to the cornea (e.g., through ablation) or to shape the posterior surface of a contact lens (or another type of optical lens) so as to achieve the required focus scatter correction. It has been found that orthogonalizing the cornea not only reduces radial focus scatter, but simultaneously reduces axial focus scatter substantially and produces more uniformity in the radius of curvature of the orthogonalized portion of the cornea.

Figure 11:
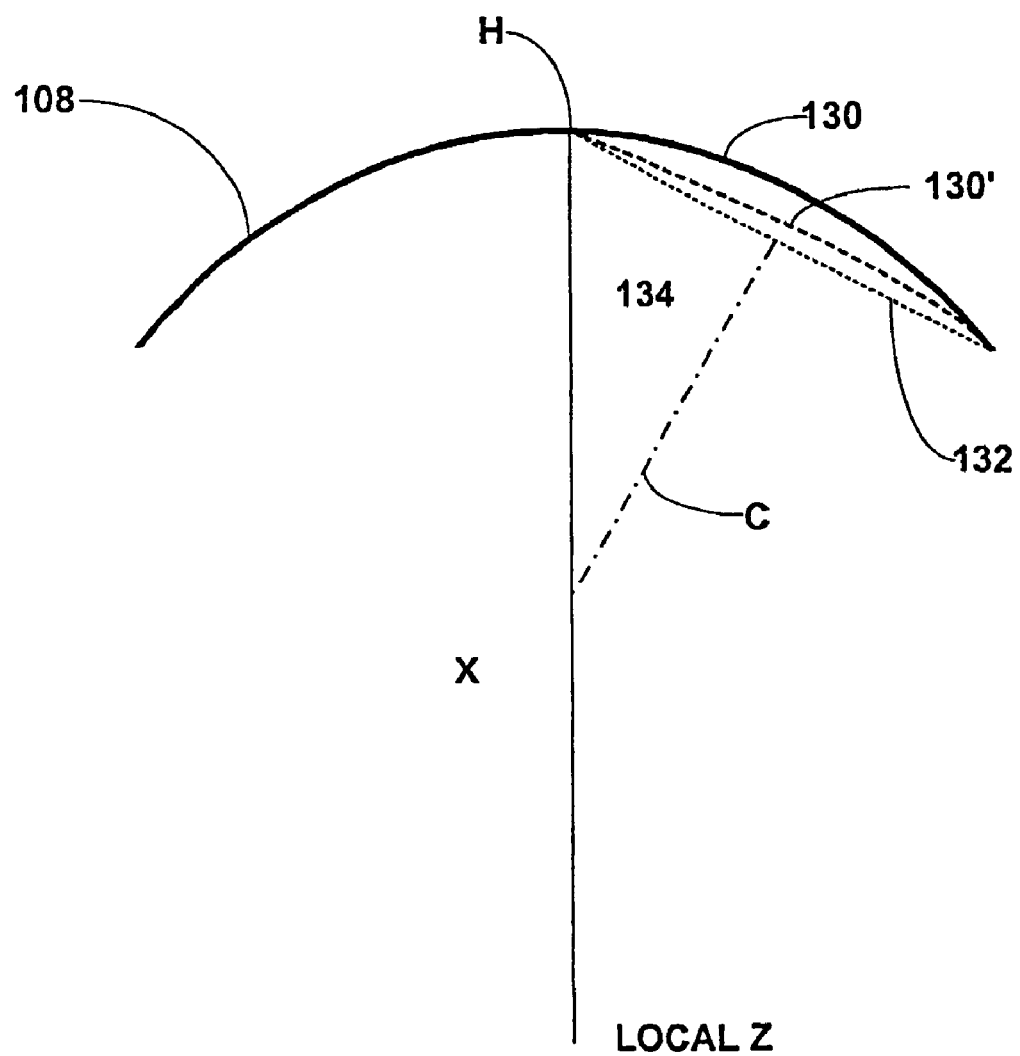
FIG. 11 illustrates a method for modifying the corneal model by orthogonalizing to the central axis.

FIG. 11 illustrates the process of orthogonalization. The process is carried out on each of the arcs which represent characteristic curves, in the manner explained below. After this piecewise refocusing, the modified arcs are reassembled into a modified surface model having the re-focused characteristics.

In FIG. 11, 130 represents one of the half-meridian arcs corresponding to a characterizing curve. Arc 130 has a center point C, the location of which has been exaggerated to demonstrate focus which is radially spaced from the LOCAL Z-AXIS. Orthogonalization of arc 130 begins with creating a chord 132 between the two ends of the arc. A perpendicular bisector 134 of chord 132 may be constructed, and it will pass through point C and intersect the LOCAL Z-AXIS at a point X. Using the distance of point X from point H (the HIGH point) as a radius, a new arc 130' can now be drawn between the two end points of arc 130. Arc 130' will be focused on the LOCAL Z-AXIS and will have a larger radius of curvature than arc 130.

At this point, arc 130' could be accepted as an arc defining the modified surface model 108'. However, it would be desirable to avoid too great a change in the thickness of the cornea. Accordingly, a certain threshold is defined (for example, 0.0075 mm), and if any portion of arc 130' is more than a distance inside or outside the surface 108, arch 130' is not accepted for use in the modified surface model. Instead, point x can be moved up or down on the LOCAL Z-AXIS (depending upon which direction arch 130' needs to be moved) by half the excess over. Arc 130' can then be re-drawn and re-tested against the threshold. This readjustment and testing continues until an acceptable arc 130' has been found. Then, the next arc is orthogonalized. After all of the arcs are orthogonalized, a new surface model 108' is created based upon all of the arcs.

As has been explained above, the orthogonalization process is applicable to corneal ablation procedures. Prior to the procedure, a corrected corneal surface model is generated, which is shaped to provide relief from macular degeneration and correction of refraction established by an eye test (as described in the patents cited above), and all the arcs are orthogonalized. The corrected corneal surface model is then registered with the unmodified corneal surface model, and it is moved towards the unmodified surface until the corrected surface just contacts the unmodified surface. If the point of initial contact is at the center of the corrected surface, it is moved toward the uncorrected surface until the periphery of the corrected surface just contacts the uncorrected surface at the diameter of the proposed ablation procedure. If the point of initial contact is at the periphery of the corrected surface, it is moved toward the uncorrected surface until the center of the corrected surface just contacts the uncorrected surface. The corrected surface will then be displaced so that it is, at least partially, inside the cornea, and the cornea is ablated until the displaced corrected surface becomes its new surface.

The central region of the retina is called the macula, and the very center of the macula, called the foveola, is the most sensitive. Although the macula typically has a diameter in the range of 6 to 7 millimeters, the central foveola typically has a diameter of about 0.35 mm. With perfect orthogonalization, all sub-portions of the cornea are refocused to the center of the macula, the foveola. When orthogonalization is performed by refocusing all of the sub-regions onto the LOCAL Z-AXIS, orthogonalization is not perfect.

In accordance with one aspect of the present invention, sub-portions of the cornea may be refocused so as to place their focal points outside the foveola yet still within the macula at a controlled lateral distance from the LOCAL Z-AXIS. The macula has approximately the shape of a cap-shaped segment of a sphere, is usually between 6 millimeter and 7 millimeters in diameter and is approximately 0.88 millimeters deep.

The difference should be kept in mind between introducing de-focus and the decentered focus of the invention. Ophthalmologists have long known that, in prescribing corrective lenses, distance focus can be reduced through de-focus, and a benefit in near vision can result. In accordance with the present invention, there is no de-focus. All sub-portions of the cornea remain fully focused, but the focus point is moved away from the LOCAL Z.

Figure 12:
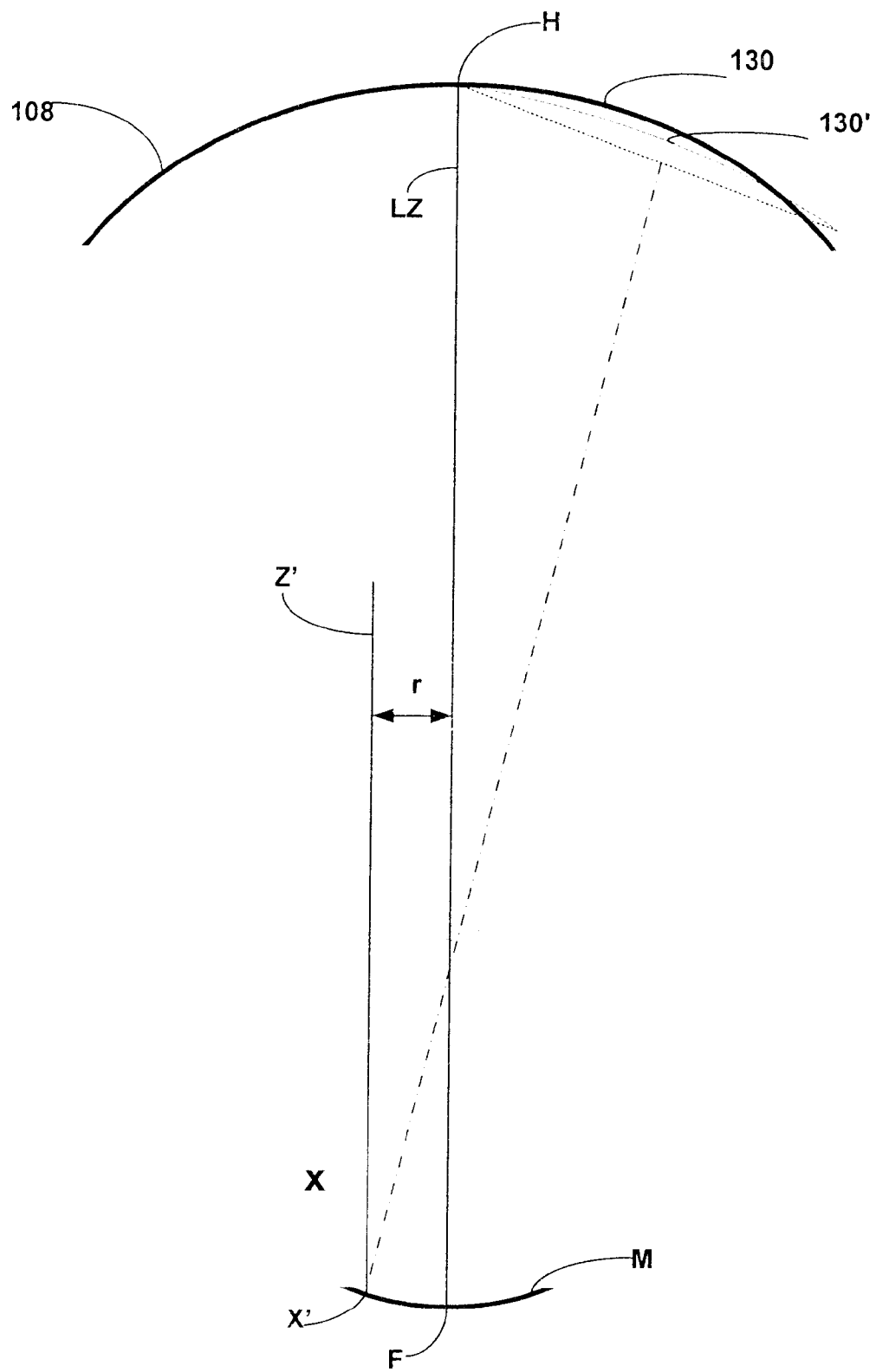
FIG. 12 illustrates the concept of decentered orthogonalization.

FIG. 12 illustrates the concept of decentered orthogonalization. The arc 130 is a sub-portion of the cornea which has a scattered focal point X. Ordinary orthogonalization as shown in FIG. 11 would move the focal point X to the LOCAL Z-AXIS, LZ. Perfect orthogonalization would move it to the foveola F on the macula M. Decentered orthogonalization creates a new arc 130''' which focuses at a point X', which is at a predefined radius r from the foveola. The axis Z' is parallel to the LOCAL Z-AXIS and passes through the point X. For purposes of estimation, the macula can be considered flat in the region between the axes LZ and Z'.

Figure 4:
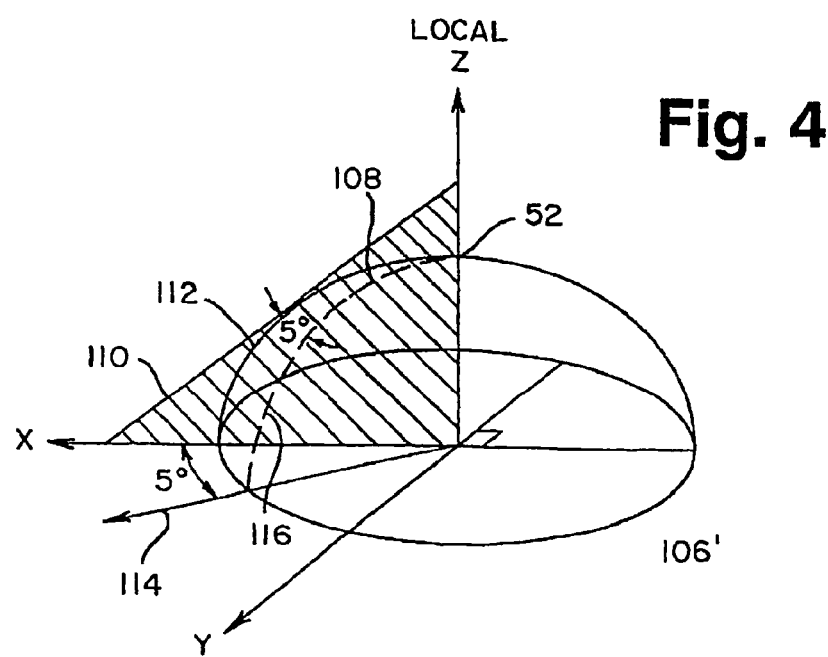
FIG. 4 is a perspective view of a cornea matching surface illustrating how characterizing curves are constructed.
Figure 13:
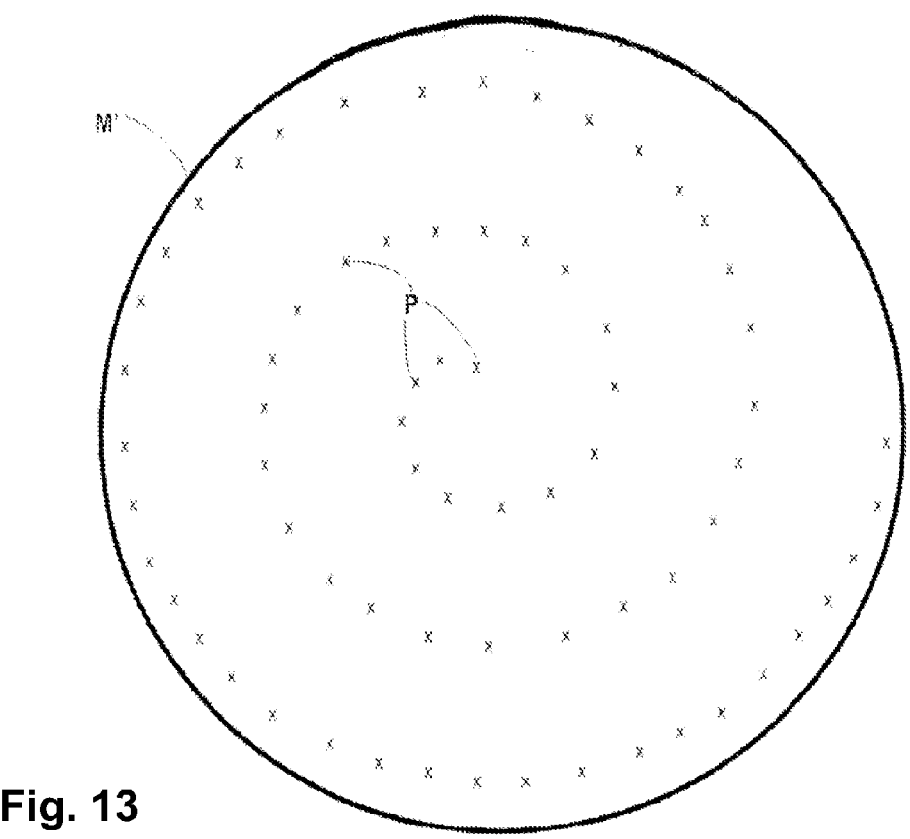
FIGS. 13-15 are plan views of the macula showing the 72 focus points P distributed in spiral, rose and dual rose patterns, respectively, on the anterior surface of the macula.

The preferred manner of performing decentered orthogonalization utilizes the technique discussed with respect to FIG. 4. Specifically, the anterior surface of the cornea is broken down into 72 arcs spaced 5° apart rotationally, and each arc is subjected to decentered orthogonalization. The 72 resulting focus points should be well distributed in a working region W' of the foveola which preferably has a diameter less than 0.07 millimeters. FIG. 13 is a top plan view of the foveola showing the 72 points P distributed in a spiral pattern on the surface of the foveola.

Figure 14:
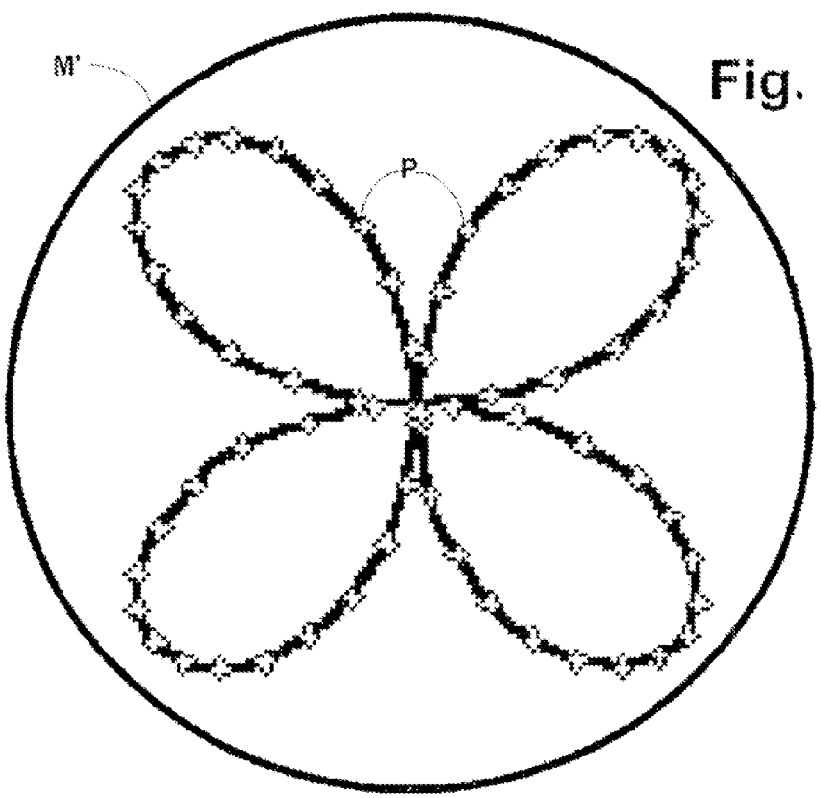
Figure 15:
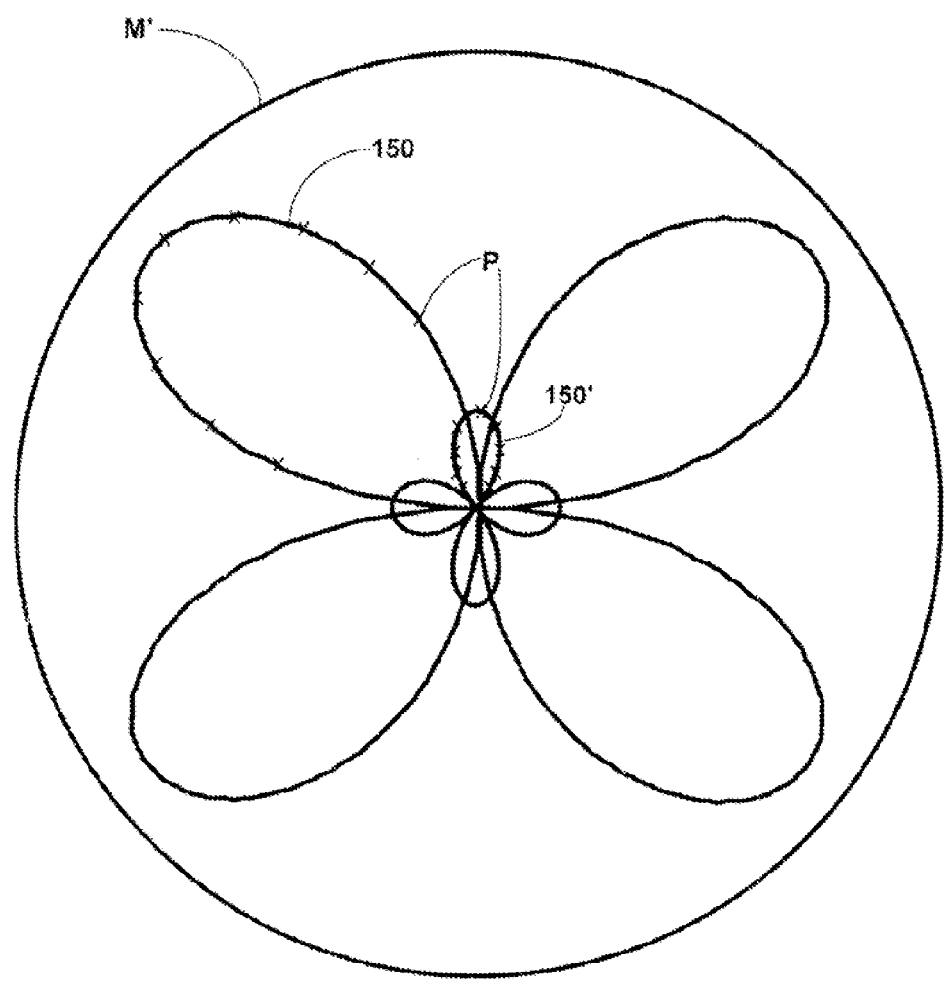

A more preferred configuration for the points is illustrated in FIG. 14. This pattern is described by the polar equation $R=a\ddot{y} \cos 2\ddot{y}$, where R is the two-dimensional radius of the point from the foveola, a is a constant selected to spread the points well over the entire working area M', and $\ddot{y}$ is the rotational angle of the particular arc on the cornea. This pattern is preferred to the spiral, because every quadrant of the working area M' has focus points at a full range of distances from the foveola.

Another preferred pattern for the focus point is illustrated in FIG. 14. In this case, the pattern is formed from two overlaid rose patterns, a large one 150 and a small one 150', which is offset by 45° from the pattern 150. Only one petal of each rose pattern is shown to have points, but it will be understood that each of the other petals is similarly provided with points. The points are shared evenly between the patterns 150 and 150'. However, the pattern 150 provides the outermost points and has points distributed at over its outermost two-thirds. Pattern 150' provides the innermost points and has them evenly distributed. As a result, the pattern in FIG. 14 provides a good distribution of points near to and distant from the foveola.

It should be appreciated that, in all the focus point patterns that have been shown, in most instances the points are equally spaced along a curve. However, those skilled in the art will appreciate that unequal spacing could be provided for the points so as to concentrate them more in a specific region (e.g., the center or the outermost area of the working region.

A further method, defining a further embodiment of the invention, has been developed for decentered orthogonalization which is preferred over all those described previously to enhance universal improvement, in some instances. This method will be referred to as "offset" decentralized orthogonalization. The method proceeds exactly as in the FIG. 11, except that once arc 130' has been reshaped, it is tilted clockwise so as to move the point X, the endpoint of the arc's axis, to the left in FIG. 11, across the local z-axis, so that it lies at a preselected distance, or offset, from the local z-axis. Biases at values below about 0.01 mm are contemplated at present, with a bias of approximately 0.0025 mm being preferred. However, distances in the range of approximately 0.0025 mm to approximately 0.01 mm still being effective.

FIG. 16 illustrates three waveforms which are useful in describing the idealized turtleback shape. Each of the waveforms is a polar graph of curvature (given in diopters) as a function of rotational position. For example, waveform A represents the cornea of an actual patient that is nearsighted, astigmatic, and exhibits age-related presbyopia. The polar angle is the rotational angle of a plane containing the local z axis (about the tilted local z axis) relative to a reference position at which the plane intersects the base of the cornea at a position closest to the nose. The curvature is the diopter equivalent of the radius of a circular arc which most closely approximates the half-meridian arc created by the intersection between the surface of the cornea and the plane when it has the particular rotational orientation. The following well-known formula relates the diopter value to the radius of the arc:

337.5/Arc Radius=Diopter Value

Ideally (for the best universal improvement of vision), waveform A should be shaped substantially like a letter "M" and it is therefore referred to herein as the "M-wave" of the cornea. It is, in the present instance, a somewhat distorted M.

As an initial step in redesigning the shape of a cornea to exhibit universal vision improvement, an idealized M-wave is generated for the cornea. Starting with a polar representation of the patient's cornea showing the surface curvature along the natural half-meridian arcs of the particular corneal surface, such as waveform A, an idealized waveform is generated. This waveform is not related to waveform A, except the lowest diopter values are preferably approximately the same in the two waveforms, but waveform B preferably meet certain criteria. However, in some instances improved vision performance may be obtained by making the baseline of waveform B 1.5 diopters higher than waveform A. First of all, the peak-to-peak diopter variation of the waveform is adjusted to be approximately 3 diopters, preferably about 2.875 diopters. It has been found that there is substantial deterioration in near vision correction if this diopter range drops below about 2 diopters or exceeds about 4 diopters. In addition, the dip D in the M-wave is adjusted so as to lie between approximately 40% and 60% of the peak-to-peak amplitude of the M-wave. Preferably, it is approximately 50%. Then, the entire waveform is adjusted so as to transition smoothly between values. Preferably, the peaks occur at about 90° and 270° and the dip at approximately 180°, while producing a smooth curve. This results in the ideal M-wave to represent the patient's cornea. This wave is represented by waveform B in FIG. 16.

As a practical matter, every lens will have the same M-wave shape, except for the adjustment to match the flattest curvature (K value) of the cornea and the necessary distance vision correction, as determined, for example, by a refraction test. K value and refraction are measurements normally taken by an eye care professional when fitting lenses and would typically be available. To customize the M-wave for a patient, it is only necessary to pick a baseline for it that corresponds to his K value and to shift the waveform vertically to provide the diopters necessary for correction of distance vision. This defines the lens shape of a custom lens for that patient.

It will be appreciated that waveform B exhibits the flattest surface curvature at 0° (a point corresponding to the edge of the cornea that would be closest to the nose in waveform B). Increasing the polar angle, the surface curvature increases continuously until it reaches a maximum at about 90° (corresponding to the vertically uppermost edge of the cornea). The surface curvature then decreases continuously until it reaches an intermediate value at about 180° (corresponding to the edge of cornea most distant from the nose), and it increases continuously to a maximum at about 270° (corresponding to the vertically lowermost edge of the cornea), and it decreases continuously until it reaches 0°, where it returns to its minimum. Thus, the surface described by this M-wave has the idealized turtleback shape discussed previously.

In the preceding paragraph it was assumed that the M wave for the patient's right eye was being considered. The reference or 0° angle was selected as the point closest to the nose and the polar angle increased in a clockwise direction. The M-wave for the left eye could be identical (i.e. with 0° at the point furthest from the nose and polar angle increasing clockwise), or it could be a mirror image of the right eye (i.e. with 0° at the nose but polar angle increasing counterclockwise). The former approach would simplify manufacture and reduce cost, since the same lens would be used for both eyes.

In some instances, better universal improvement of vision will be attained if the surface model represented by waveform B is provided with one additional adjustment. That is, if offset, decentered orthogonalization is performed on the surface model with an offset of less than approximately 0.005 mm from the local z axis. Most preferably, the offset is about 0.0025 mm. The upper offset limit of 0.005 mm was selected because experimentation has shown that a significant deterioration in distance or near vision is reached at that value. Distance vision continues to deteriorate significantly as offset is increased further.

In one embodiment, the surface model represented by waveform B, represents the shape of the posterior surface of a contact lens for use by the patient. In accordance with the present invention, the shape of the anterior surface of the lens is derived by providing a diopter adjustment along waveform B which is determined to be necessary to correct the patient's distance vision. Typically, such diopter correction would be determined from a conventional refraction test. At each angle, the anterior surface diopter value Da and radius Ra are determined by the Zeiss lens formulas:

$$Da=(-P\,Dp)/(1-(((T/1000)/Na)*Dp))$$

$$Ra=(N_L-N_A)*1000/Da$$

where
    Da is the diopter value of the anterior arc
    Dp is the diopter value of the posterior arc
    $N_L$ is the index of refraction of the material of which the lens is made
    $N_A$ is the index of refraction of air
    P is the power adjustment factor, and
    T is the lens thickness.

Following this diopter adjustment, waveform C results.

Those skilled in the art will appreciate that the posterior surface of the contact lens need not be shaped as defined by waveform B. In fact, it could be any shape calculated to conform generally to the patient's cornea, such as a spherical surface or an ellipsoidal surface. The idealized M wave is a turtleback shape, not spherical or ellipsoidal and, except for preferably having the same minimum curvature as the cornea, is universal and has no relationship to the patient's native cornea. Moreover, matching the flattest curvature of the cornea is not related to vision correction, but is done to assure that the lens will have a more comfortable fit.

When the lens is placed on the eye, the lens, the cornea and the tear film therebetween will have substantially the same index of refraction. Thus, only the interface between the air and anterior surface of the lens will have a significant effect on vision improvement. Using a surface shape defined by waveform B for the posterior surface of the lens minimizes unnecessary thickness variation in the lens, which can introduce certain distortions.

Those skilled in the art will appreciate that the surface model represented by waveform C could also be used to define the desired shape of the cornea following a surgical procedure. The surgical procedure constitutes an actual reshaping of the cornea, while the use of the contact lens constitutes an effective reshaping.

It should be appreciated that the contact lens described immediately above is a custom designed contact. However, it is contemplated that M-wave lenses could be provided in ready-made prescription form as in current mass produced lenses. For example, in the case where a lens has an M-wave posterior surface, lenses could be provided in different base curvature variations or "sizes" (e.g. a large base curve for a relatively flat cornea, a medium for a cornea of medium or average curvature, and a small for a relatively steeply shaped cornea). In all cases, the M-wave has the idealized shape described earlier, so the only difference between the sizes is the actual values of the initial curvature. Each posterior curve set would include a subset of lenses with different anterior curves such that each size would include a subset of lenses with the necessary diopter adjustment to correct for different distance refractive errors. The patient would only require two optometric tests in order to obtain the correct prescription. First, the optometrist would perform a conventional refraction test to determine the diopter correction required for distance vision. Second, during the initial visit the optometrist or lens fitter also could perform a conventional keratometer test, which yields the diopter readings for the flattest and steepest portions of the cornea. The flattest curvature of the keratometer test determines whether the patient needs a lens with a small, medium, or large posterior surface base curve (in order to obtain best fit), and the refraction test establishes the required distance correction. Given this prescription, an eye care professional could easily fit the patient with the most comfortable M-wave lens that will provide universal vision improvement.

Although preferred embodiments of the invention have been disclosed for illustrative purposes, those skilled in the art will appreciate that many additions, modifications, and substitutions are possible without departing from the scope and spirit of the invention. For example, the present invention is applicable not only to corneal ablation and contact lenses, but to any other kind of lens, including cataract, phakic, intraocular, intracorneal and spectacle lenses.

What is claimed:

1. An optical lens having anterior and posterior surfaces and an optical center on its anterior surface, the anterior surface having an M-wave shape such that the surface curvature measured along a curve passing through the optical center varies substantially as a smoothed letter M in relationship to angular orientation about the optical center, where 0° angular orientation is substantially the point closest to the nose when the lens is worn and the central dip of the M occurs substantially at a point which is furthest from the nose when the lens is worn, corresponding to a 180° orientation, there being maxima of the M at substantially the uppermost and lowermost vertical extremes of the lens when it is worn, to 90° and 270° orientations, respectively.

2. The lens of claim 1 wherein a baseline of the M-wave occurs at a value determined by the K value of eye of the patient to wear the lens.

3. The lens of claim 2, wherein the M-wave further includes a vertical shift relative to the baseline which is related to a required distance vision correction for the patient.

4. The lens of claim 1, wherein the M-wave further includes a vertical shift relative to a baseline which is related to a required distance vision correction for the patient.

5. The lens of any one of claim 1-3 or 4, wherein the posterior surface exhibits a shape other than an M-wave shape.

6. The lens of claim 1, wherein the amplitude of the M-wave corresponds to curvature between approximately 2 and approximately 4 diopters.

7. The lens of claim 6, wherein the amplitude of the M-wave corresponds to curvature of approximately 3 diopters.

8. The lens of claim 6, wherein the amplitude of the M-wave corresponds to curvature of approximately 2.85 diopters.

9. The lens of claim 6, wherein the dip in amplitude of the M-wave is between approximately 40% and approximately 60% of the peak-to-peak amplitude of the M-wave.

10. The lens of claim 9, wherein the dip in amplitude of the M-wave is approximately 50% of the peak-to-peak amplitude of the M-wave.

11. The lens of any one of claim 1-3 or 4, wherein the dip in amplitude of the M-wave is between approximately 40% and approximately 60% of the peak-to-peak amplitude of the M-wave.

12. The lens of claim 11, wherein the dip in amplitude of the M-wave is approximately 50% of the peak-to-peak amplitude of the M-wave.

13. An optical lens for improving the vision of an eye, the lens comprising areas of focus on a surface thereof corresponding to different locations on the corneal surface of the eye, each area of focus being shaped to shift the focus of the corresponding location of the cornea to a predetermined location relative to a predefined reference axis in the eye, without forcing the focus of each area to a common point, a plurality of points of focus being shifted so as to form a predefined pattern on the retina of the eye, wherein the predetermined pattern is one of a circle, a spiral, a rose pattern and a dual rose pattern.

14. The lens of claim 13 wherein the lens comprises one of a cataract lens, a phakic lens an intraocular lens, an intracorneal lens and a spectacle lens.

15. The lens of claim 13 wherein the reference axis passes through the HIGH point.

16. The lens of any one of claims 13-15 wherein the reference axis is the LOCAL Z AXIS.

17. The lens of any one of claim 1-3 or 4, wherein the posterior surface exhibits an M-wave shape.

* * * * *